(12) United States Patent
Shideler et al.

(10) Patent No.: US 10,722,149 B2
(45) Date of Patent: Jul. 28, 2020

(54) REAL-TIME BIOFEEDBACK REHABILITATION TOOL GUIDING AND ILLUSTRATING FOOT PLACEMENT FOR GAIT TRAINING

(71) Applicants: Blynn Shideler, Gibsonia, PA (US); Simon Taylor, Mernda (AU); Rezaul Begg, Blackburn North (AU)

(72) Inventors: Blynn Shideler, Gibsonia, PA (US); Simon Taylor, Mernda (AU); Rezaul Begg, Blackburn North (AU)

(73) Assignee: VICTORIA UNIVERSITY, Footscray (AU)

( * ) Notice: Subject to any disclaimer, the term of this patent is extended or adjusted under 35 U.S.C. 154(b) by 144 days.

(21) Appl. No.: 15/660,039

(22) Filed: Jul. 26, 2017

(65) Prior Publication Data

US 2017/0360333 A1   Dec. 21, 2017

(51) Int. Cl.
*A61B 5/11*       (2006.01)
*A61B 5/103*      (2006.01)
(Continued)

(52) U.S. Cl.
CPC ............. *A61B 5/112* (2013.01); *A61B 5/1038* (2013.01); *A61B 5/1126* (2013.01); *A61B 5/22* (2013.01);
(Continued)

(58) Field of Classification Search
CPC ..... A61B 5/1128; A61B 5/1127; A61B 5/112; A61B 5/1038; A63B 24/0062; A63B 71/0622; A63F 13/21
See application file for complete search history.

(56) References Cited

U.S. PATENT DOCUMENTS 6,645,126 B1 *  11/2003  Martin ............... A63B 69/0059
                                                     482/3
9,526,451 B1 *  12/2016  Berme ................... A61B 5/486
(Continued)

OTHER PUBLICATIONS

Teran-Yengle et al., "Short and long-term effects of gait retraining using real-time biofeedback to reduce knee hyperextension pattern in young women" p. 948-952, Dec. 2011, vol. 41, No. 12, journal of orthopaedic & sports physical therapy.
(Continued)

*Primary Examiner* — Eric J Messersmith
(74) *Attorney, Agent, or Firm* — Blynn L. Shideler; Krisanne Shideler; BLK Law Group

(57) ABSTRACT

A biofeedback rehabilitation display for gait training visible to the subject including a plurality of foot placement targets visible to the subject on the display and moving along the display at a speed proportional to the desired gait speed of the subject and in a direction along the display representative of the direction of locomotion of the subject; a pair of subject foot icons visible to the subject illustrating real-time foot positioning of the subject throughout the gait pattern of the subject, wherein the foot icons distinguish between stance phase and swing phase throughout the gait pattern of the subject; and at least one real-time proximity measurement visible to the subject for each stance phase providing the subject with an indication of the proximity of each stance phase of each foot with an intended foot placement target.

19 Claims, 1 Drawing Sheet

(51) Int. Cl.
   *A61B 5/00*    (2006.01)
   *G06F 19/00*   (2018.01)
   *A61B 5/22*    (2006.01)
   *A63B 22/02*   (2006.01)

(52) U.S. Cl.
   CPC .......... *A61B 5/742* (2013.01); *G06F 19/3481* (2013.01); *A61B 5/222* (2013.01); *A63B 22/02* (2013.01)

(56) References Cited

U.S. PATENT DOCUMENTS

| | | | |
|---|---|---|---|
| 2004/0009845 A1* | 1/2004 | Johnson | A63B 23/0464 482/41 |
| 2012/0021873 A1* | 1/2012 | Brunner | A63B 22/0235 482/9 |

OTHER PUBLICATIONS

Van Ooijen et al. The efficacy of treadmill training with and without projected visual context for improving walking ability and reducing fall incidence and fear of falling in older adults with fall-related hip fracture: a randomized controlled trial, 2016, 6:215, BioMed Central.

* cited by examiner

REAL-TIME BIOFEEDBACK REHABILITATION TOOL GUIDING AND ILLUSTRATING FOOT PLACEMENT FOR GAIT TRAINING

BACKGROUND OF THE INVENTION

Field of the Invention

The present invention relates to gait training with biofeedback, more particularly to a real-time biofeedback rehabilitation tool or display for guiding and illustrating foot placement for gait training.

Background Information

Gait analysis is the systematic study of animal locomotion, more typically in the context of this application the study of human motion. Generally in modern times gait analysis uses instrumentation for measuring body movements, body mechanics, and the activity of the muscles. Gait analysis is used to assess and treat individuals with conditions affecting their ability to walk. It is also commonly used in sports biomechanics to help athletes run more efficiently and to identify posture-related or movement-related problems in people with injuries.

The pioneer of scientific gait analysis may be said to be Aristotle with his work entitled *De Motu Animalium* (On the Gait of Animals). A much later fellow pioneer of gait analysis was Giovanni Alfonso Borelli with his 1680 work also called *De Motu Animalium* (I et II). In the 1890s, the German anatomists Christian Wilhelm Braune and Otto Fischer published a series of papers on the biomechanics of human gait under loaded and unloaded conditions.

Photography and cinematography advancements permitted the capture of image sequences revealing details of human and animal locomotion that were not noticeable by watching the movement with the naked eye. Eadweard Muybridge and Etienne-Jules Marey were pioneers of these technological developments leading, for example, to revealing the detailed sequence of the horse "gallop", which was usually misrepresented in paintings made prior to this discovery. In the world of literature Arthur Conan Doyle has Sherlock Holmes utilizing gait analysis to calculate and identify the height of the Rache killer in "A Study in Scarlet."

The widespread application of gait analysis to humans with pathological conditions such as cerebral palsy, Parkinson's disease, and neuromuscular disorders, effectively began in the 1970s. The development of treatment regimes based on gait analysis results advanced significantly in the 1980s. Many leading orthopedic hospitals worldwide now have gait labs that are routinely used to design treatment plans, such as gait training, and for follow-up monitoring.

Research has shown that gait training with biofeedback has a much greater effect than treadmill walking without biofeedback. Several methods of providing biofeedback have been utilized to supplement treadmill training in gait rehabilitation. For example, a study at the University of Iowa aimed to use biofeedback to reduce knee hyperextension in young women by providing patients with a real-time knee angle plot and a virtual target knee angle at heel-strike. See Teran-Yengle et al. (2016) "Short and long-term effects of gait retraining using real-time biofeedback to reduce knee hyperextension pattern in young women" *Gait & Posture*. Other researchers have employed techniques using physical targets, such as light projections on a treadmill to mark targets for foot placement during treadmill training. See Van Ooijen et al. (2016) "The efficacy of treadmill training with and without projected visual context for improving walking ability and reducing fall incidence and fear of falling in older adults with fall-related hip fracture: a randomized controlled trial" *BMC Geriatrics*.

There remains a need in the art for efficient and effective real-time biofeedback rehabilitation tool or display for guiding and illustrating foot placement for gait training which still allows subjects or patients to best simulate a real-world walking conditions during at least treadmill training.

SUMMARY OF THE INVENTION

The present invention addresses the deficiencies of the prior art and provides a real-time biofeedback rehabilitation tool or display guiding and illustrating foot placement for gait training.

One aspect of the present invention provides a biofeedback rehabilitation display for gait training visible to the subject including a plurality of foot placement targets visible to the subject on the display and moving along the display at a speed proportional to the desired gait speed of the subject and in a direction along the display representative of the direction of locomotion of the subject; a pair of subject foot icons visible to the subject illustrating real-time foot positioning of the subject throughout the gait pattern of the subject, wherein the foot icons distinguish between stance phase and swing phase throughout the gait pattern of the subject; and at least one real-time proximity measurement visible to the subject for each stance phase providing the subject with an indication of the proximity of each stance phase of each foot with an intended foot placement target.

The biofeedback rehabilitation display for gait training according to one aspect of the invention provides that a stance phase is determined by the detection of a heel strike of the subject and the real-time proximity measurement is determined by the radial distance from a fixed point of the stance phase foot position to a fixed point on the nearest foot placement target.

The biofeedback rehabilitation display for gait training according to one aspect of the invention provides that the real-time proximity measurement visible to the subject includes a visible indication when the proximity measurement is less than an acceptable threshold, and wherein the real-time proximity measurement visible to the subject includes a visible indication when the proximity measurement is greater than an unacceptable threshold. Further the invention may provide wherein the real-time proximity measurement visible to the subject includes a visible indication when the proximity measurement is between the acceptable threshold and the unacceptable threshold.

The biofeedback rehabilitation display for gait training according to one aspect of the invention may provide that the foot placement target includes a visible representation of an associated proximity measurement.

The biofeedback rehabilitation display for gait training according to one aspect of the present invention may provide wherein the real-time proximity measurement visible to the subject for each stance phase provides the subject with an indication of the proximity of each stance phase with an intended foot placement target in both the direction of locomotion of the subject and lateral to the direction of locomotion of the subject.

The biofeedback rehabilitation display for gait training according to the invention may provide wherein a stance phase is determined by the detection of a heel strike of the subject and the stance phase illustrates foot orientation of the subject's foot at the time of the detected heel strike or otherwise during the stance phase. Further the invention may provide a visual indication of the difference between the measured foot orientation of the subject's foot and the target foot orientation of the subject's foot.

The biofeedback rehabilitation display for gait training according to one aspect of the invention may further include an audio component of the real-time proximity measurement which is audible to the subject.

The biofeedback rehabilitation display for gait training according to one aspect of the invention may provide wherein the speed of the foot placement targets is derived from a treadmill coupled to the display and wherein the speed of the foot placement targets is variable.

The biofeedback rehabilitation display for gait training according to one aspect of the invention provides that the real-time foot positioning of the subject throughout the gait pattern of the subject is obtained through motion capture software, and wherein the motion capture software tracks position markers placed on the pelvis, lower limbs, and feet of the subject monitored by cameras.

The biofeedback rehabilitation display for gait training according to one aspect of the invention provides wherein the spacing between adjacent foot placement targets visible to the subject is adjustable. Further the spacing between adjacent foot placement targets visible to the subject may vary for one subject to train gait adaptability, wherein the variance of the spacing between adjacent foot placement targets visible to the subject for training gait adaptability include variance in mediolateral position and spacing in the direction of locomotion.

The biofeedback rehabilitation display for gait training according to one aspect of the invention further includes the display of virtual obstacles visible to the subject on the display and moving along the display at a speed proportional to the desired gait speed of the subject and in a direction along the display representative of the direction of locomotion of the subject. Further, the invention may provide for including the display of real-time proximity measurements visible to the subject for each virtual obstacle associated with a degree of avoidance of the virtual obstacle.

These and other aspects of the invention are described throughout this specification.

BRIEF DESCRIPTION OF THE FIGURES

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted in connection with the attached figures. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope. The terms "a" and "an" herein do not denote a limitation of quantity, but rather denote the presence of at least one of the referenced items.

Figure 1:
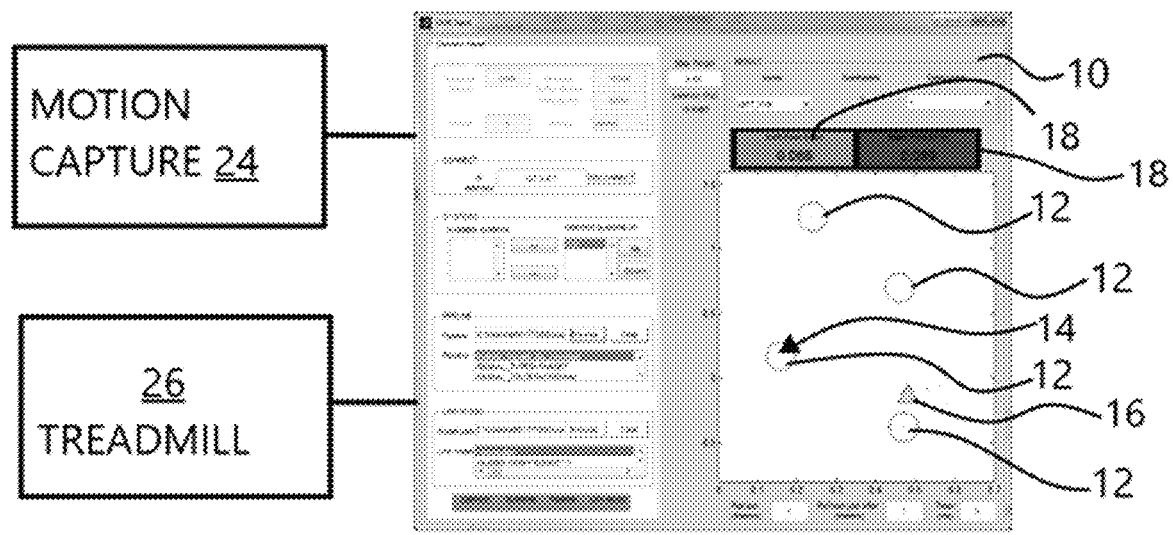
FIGS. 1 and 2 are schematic representations of a real-time biofeedback rehabilitation tool or display for guiding and illustrating foot placement for gait training according to the present invention.
Figure 2:
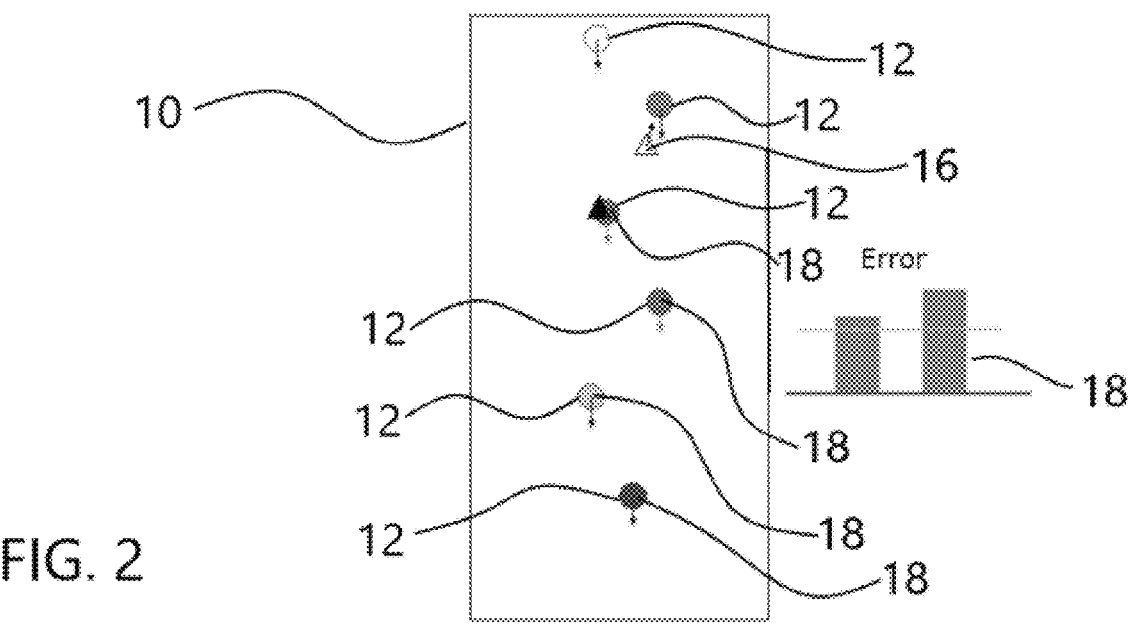

The present invention describes a biofeedback rehabilitation tool or display 10 for gait training. The term display 10 used herein references what may be visible to the subject as shown in FIG. 2 as well as what may be visible to the clinician (or technician) as shown in FIG. 1 (the clinician screen may have more controls visible than visible to the subject), as well as the software and hardware (the computer) associated with calculating, creating and manipulating the visible components of the display 10 visible to the subject and/or the clinician/technician. The tool or display 10 may be effectively implemented on a conventional laptop computer with a separate display unit (monitor or second screen) mounted in view of the subject.

The display 10 according to the invention includes a plurality of foot placement targets 12 visible to the subject on the display 10 and moving along the display 10 at a speed proportional to the desired gait speed of the subject and in a direction along the display 10 representative of the direction of locomotion of the subject. The motion of the targets 12 on the display 10 is shown by arrows in FIG. 2 and generally they will flow down the screen or field of the display 10. The desired gait speed may come from a controllable treadmill 26 as discussed below.

The display 10 includes a pair of subject foot icons 14, 16 visible to the subject illustrating real-time left and right foot positioning of the subject throughout the gait pattern of the subject, wherein the foot icons 14, 16 distinguish between stance phase 14 and swing phase 16 throughout the gait pattern of the subject.

The display 10 includes at least one real-time proximity measurement 18 visible to the subject for each stance phase foot icon 14 of each foot providing the subject with an indication of the proximity of the stance phase foot icon 14 with an intended foot placement target 12.

The gait pattern of the subject within this application references the repetitive gait of the subject throughout the training episode. The subject's gait cycle is the repetitive component of the subject's gait pattern. The gait cycle may be considered as involving steps and strides wherein a step is one single step, and a stride is a whole gait cycle. The step time is the time from one foot hitting the floor/ground to the other foot hitting the floor/ground. Step width can be described as the mediolateral space between the two feet.

One classification of the gait cycle involves two main phases: the stance phase (represented by icon 14) and the swing phase (represented by icon 16). These phases can be grouped into eight distinct phases: Heel Strike or Initial Contact, Flat Foot or Loading Response, Mid-stance, Heel Off or Terminal Stance, Toe Off or Pre Swing, Initial Swing, Mid Swing and Late Swing or Declaration. There are other acceptable breakdown or classification schemes of the gait cycle and this grouping is chosen merely for illustrative purposes.

Heel strike, also known as initial contact, is a short period which begins the moment the foot touches the ground and is the first phase of double support and is the first stance phase. Generally about 30° flexion of the hip and full extension in the knee is observed. The ankle moves from a neutral (supinated about 5°) position into plantar flexion. After this, knee flexion (about 5°) begins and increases, just as the plantar flexion of the heel increased. The plantar flexion is allowed by eccentric contraction of the tibialis anterior, extension of the knee is caused by a contraction of the quadriceps, flexion is caused by a contraction of the hamstrings, and the flexion of the hip is caused by the contraction of the rectus femoris. As discussed below the foot icon 14 will be displayed at the calculation of the heel strike of the subject, with the foot icon 14, 16 changing from the visible icon 16 for that foot (left or right) representation to the icon 14 for that foot (left or right) representation based upon the phase change.

In foot flat, or loading response phase, the body absorbs the impact of the foot by rolling in pronation and this is a stance phase. The hip moves slowly into extension, caused by a contraction of the adductor magnus and gluteus maximus muscles. The knee flexes to about 15° to 20° of flexion and ankle plantar flexion increases to about 10-15°. The foot icon 14 will be displayed throughout the foot flat, or loading response phase.

In mid-stance, a stance phase, the hip moves from about 10° of flexion to extension by contraction of the gluteus medius muscle. The knee reaches maximal flexion and then begins to extend. The ankle becomes supinated and dorsiflexed (about 5°), which is caused by some contraction of the triceps surae muscles. During this stance phase, the body is supported by one single leg. At this moment the body begins to move from force absorption at impact to force propulsion forward. The foot icon 14 will be displayed throughout the mid-stance phase.

Heel off or terminal stance phase begins when the heel leaves the floor. In this stance phase, the body weight is divided over the metatarsal heads. Typically about 10-13° of hip hyperextension is present, which then goes into flexion. The knee becomes flexed (up to about 5°) and the ankle supinates and plantar flexes. The foot icon 14 will be displayed throughout the Heel off or terminal stance phase.

In the toe-off or pre-swing phase, the hip becomes less extended. The knee is flexed about 35-40° and plantar flexion of the ankle increases to about 20°. In toe-off, like the name says, the toes leave the ground and this phase marks the transition between stance phase and swing phase with the foot icon 14, 16 changing from the visible icon 14 for that foot (left or right) representation to the icon 16 for that foot (left or right) representation based upon the phase change.

In the early swing phase (the first full swing phase) the hip extends to 10° and then flexes due to contraction of the iliopsoas muscle to about 20° with lateral rotation. The knee flexes to about 40-60°, and the ankle goes from about 20° of plantar flexion to dorsiflexion, to end in a neutral position. The foot icon 16 will be displayed throughout the early swing phase.

In the mid swing phase, which is a swing phase, the hip flexes to about 30° via contraction of the adductors, and the ankle becomes dorsiflexed due to a contraction of the tibialis anterior muscle. The knee flexes about 60° but then extends approximately 30° due to contraction of the sartorius muscle. This extension is caused by the quadriceps muscles. The foot icon 16 will be displayed throughout the mid swing phase.

The late swing or declaration phase begins with hip flexion of about 25-30°, a locked extension of the knee and a neutral position of the ankle. The late swing phase is a swing phase of the gait cycle. The foot icon 16 will be displayed throughout the late swing or declaration phase.

The display 10 of the present invention may visibly indicate any or all of the above individual identified gait phases if such labeling or indication is deemed relevant or helpful to the subject or to the technician/clinician. However, in the vast majority of practical applications of the present invention differentiating between the stance phase 14 and the swing phase 16 via changes in the subject's foot icon 14 or 16 is sufficient. The visible differentiation is easily accomplished by changing the visible shading of the interior of the icon 14 or 16 between the stance phase icon 14 and the swing phase icon 16 (including having a shaded and unshaded icon 14 and 16).

A variety of icon shapes such as a foot profile, a rectangle or an oval, could be used for icons 14 or 16, but a triangle represents a useful and simple representative icon, because it can easily convey foot position to the subject and more accurately or effectively convey angular position of the foot to the subject where needed. (as discussed below).

A variety of visible indicia could be used for targets 12 including a moving horizontal line, but a circular or oval icon as shown is preferred as it represents a simple easily understood indicia that can also convey lateral target positioning if desired, as may become important for training gait adaptability of the subject. The targets 12 could include further indicia to indicate desired or target foot orientation, such as a bisecting line orientated along the target foot orientation direction, or the shape itself such as the oval could be orientated in the target foot orientation where the shape 12 has an easily identifiable longitudinal direction.

As discussed herein the biofeedback rehabilitation display 10 for gait training according to the present invention incorporates successful biofeedback protocols while still allowing subjects to best simulate a real-world walking conditions during treadmill training in a general heads up environment similar to natural walking. The real-time biofeedback rehabilitation tool or display 10 may effectively be used for training gait adaptability. The display can be easily and effectively implemented in both clinical and research settings as a rehabilitation device and a data analysis tool. The display 10 may be described as a program that displays real-time foot position via icons 14 and 16 during walking.

The display 10 requires data input from real-time motion capture software 24, such as Vicon Nexus, OptiTrack, or Codamotion software. Specifically the display 10 may be implemented using data from position markers place on the pelvis, lower limbs, and feet, tracked by the motion capture software 24, to provide subject and clinician with a real-time visual of the subject's foot position, shown as icons 14 and 16 in the display 10. Thus, if the location of the subject (and treadmill 26 if used) is considered to be a standard Cartesian coordinate system, subjects can observe their feet move in the X-Y Cartesian plane in real-time throughout their gait cycle via icons 14 and 16. As should be understood each foot icon (the left and right) will switch between being a stance phase 14 and the swing phase 16 as each respective foot moves between the stance phase and the swing phase in the subject's gait cycle.

Additionally, the display 10 uses the motion capture 24 data to display the angle of the foot via icon 14 or 16 in the X-Y Cartesian plane by the direction of the top of the triangle shaped icon. Where angle of the subject's foot is a critical component of the training, an optional extra line could extend from the triangle icon 14 or 16 to further, more clearly, show this orientation. For example, such illustration of foot orientation (together with a target foot orientation included in targets 12) may be a useful feature for rehabilitation of pigeon-toed/duck-footed walking of the subject.

The display 10 trains gait adaptability and foot placement during treadmill training by providing subjects with virtual targets 12 and possibly obstacles that stream down the display 10 at treadmill or gait speed. Obstacles are not shown in the figures for clarity, but would be preferable an icon that is visibly different from the targets 12, such as a square with an X through the square, or a stop sign shape or other shape easily distinguished by subjects from the target 12 shape. Where virtual obstacles are utilized the biofeedback rehabilitation display 10 for gait training may include the display of real-time proximity measurements visible to the subject for each virtual obstacle associated with a degree of avoidance of the virtual obstacle, such as color coding the obstacles as green for those successfully avoided and red for those not successfully avoided by the subject.

To train gait, subjects are instructed to step on virtual targets 12 (and avoid virtual obstacles, if used). Subjects receive biofeedback in real-time on the accuracy of their foot placement on each step with respect to the targets 12 (and obstacles, if used) by a visible real-time proximity measurement 18 all visible to the subject on the display 10. Treadmill training allows for easy implementation of a monitor mounted on the front of the treadmill facing the subject to form the display 10 visible to the subject, with the monitor coupled to a laptop which may have a separate display with controls visible to the clinician. The real-time proximity measurement 18 shown is determined by the radial distance from a fixed point of the stance phase foot 14 position to a fixed point on the nearest foot placement target 12. The figures show three distinct proximity measurement 18 for the display 10.

In FIG. 1 the measurement 18 is separated into two rectangles displaying the results for the current left and right stance phase 14 of the subject in the form of a numerical calculation of the proximity measurement and a color coding of the rectangular display area. The color coding can be green for measurements below a select lower acceptable threshold, yellow for measurements above the lower acceptable threshold and below an upper unacceptable threshold, and red for measurements above the higher unacceptable threshold.

In FIG. 2 there are two distinct types of measurements 18. The first type of measurement 18 displayed in FIG. 2 is in a bar chart on the right side of the display 10 for the current left and right stance phase 14 of the subject in the form of a left and right bar graph corresponding to the measurement relative to the target 12, represented by a line across the bar graph. This bar graph format is helpful if the step length in the direction of locomotion is important, and particularly where the additional information of too short or too long of a step is important. The total height of the bar graph will be the distance from the base of the graph to the line representing the target 12 position and + the measurement 18 for steps beyond the target (too long) or − the measurement 18 for steps prior to the target 12 (too short). The bar itself can include the color coding (Green, Yellow, Red) discussed above in connection with the measurement 18 shown in FIG. 1, namely a green bar is acceptable error range, red is unacceptable error range and yellow is in between.

The second type of measurement 18 shown in FIG. 2 is where the foot placement target 12 includes a visible representation in the interior of an associated proximity measurement, specifically the color coding of the interior of the target 12 (Green, Yellow, Red) discussed above in connection with the measurement 18 shown in FIG. 1. This will give the subject feedback on foot placement accuracy of the last few steps visible on the display 10.

It is anticipated that the training episode may be recorded for playback or review or analysis by the subject and/or the clinician as desired.

Further the biofeedback for measurements 18 may include audible feedback. For example a positive sound like a bell for measurements below a select lower acceptable threshold, no sound for measurements above the lower acceptable threshold and below an upper unacceptable threshold, and a negative connotation sound like a buzzer for measurements above the higher unacceptable threshold.

Reiterating the particulars of the measurement 18, each time a heel-strike for a subject's foot is detected, the icon for that foot will indicate the stance phase 14 of the subject for that foot and the display 10 calculates the error vector between the foot position 14 and the nearest target 12. That target 12 updates its color to indicate the accuracy of the foot placement (green if the error was within a small margin, yellow if within a larger margin, otherwise red). Further, each error margin associated with a color may also be associated with a sound that plays at each heel-strike. Thus, the display may provide subjects with both auditory and visual feedback on the accuracy of their walking during treadmill training, as both auditory and visual biofeedback have shown improvement in the efficacy of treadmill training.

The display 10 may be used to train a variety of subjects within a wide range of gait abilities from young, healthy subjects to subjects with limited mobility. An easier setting or training episode could display targets 12 spaced evenly in both the mediolateral and forward directions to train a consistent gait pattern, useful for elderly subjects in rehabilitation. A more difficult setting or training regime could display targets 12 that appear at varying or random mediolateral positions and at varying step-length separations, useful for training gait adaptability for a changing environment.

The display 10 uses motion capture software that may be formed, for example, as the integration of Vicon Nexus™ motion capture software, C-Motion's Visual3D™ biomechanics modeling software, and Matlab's GUIDE™ Graphical User Interface software. The motion capture software may use cameras and position markers placed on the pelvis, lower limbs, and feet to track real-time position of the subject. In this implementation the data from Vicon Nexus™ brand motion capture components is sent to C-Motion's Visual3D™ Server where data is stored in real-time and a human model is built for the subject to ensure precise body positions. Data is sent from Visual3D™ Server in real-time to the biofeedback display 20, designed as a Matlab's GUIDE Graphical User Interface. Targets 12 and error or proximity computations 18 are all produced in Matlab.

The biofeedback rehabilitation display 10 for gait training according to one aspect of the invention may provide wherein the real-time proximity measurement 18 visible to the subject for each stance phase 14 provides the subject with an indication of the proximity of each stance phase foot 14 with an intended foot placement target 12 in both the direction of locomotion of the subject and lateral to the direction of locomotion of the subject. Basically separating out the X and Y proximity for each phase.

As noted above the stance phase 14 is determined by the detection of a heel strike of the subject and the triangular icons allows the stance phase 14 to easily and effectively illustrate foot orientation of the subject's foot at the time of the detected heel strike and throughout the stance phase 14. Where orientation is important the display 10 of the invention further can include a visual indication of the difference between the measured foot orientation of the subject's foot and the target foot orientation of the subject's foot.

As noted above the biofeedback rehabilitation display 10 for gait training according to one aspect of the invention provides that the speed of the foot placement targets 12 is derived from a treadmill 26 (such as available from Treadmetrix) coupled to the display 10 and wherein the speed of the foot placement targets 12 is variable based upon the speed of the treadmill 26 defining the speed of the subject's gait. The use of the treadmill 26 allows the display 10 to be formed as a monitor mounted on the treadmill 26 directly in front of the subject such that the display 10 easily permits the heads up orientation of the subject during training.

The present invention is not expressly limited to implementation with a treadmill 26 but could be used with force plates found in many gait labs or in other environments in which the gait of the subject can be effectively tracked. With or without a treadmill, the display 10 could be formed as a projection on a wall large enough for the subject to see throughout the walking path. With or without a treadmill the display 10 could be presented to the user on a heads up type goggle display worn by the subject. With or without a treadmill the display 10 could be presented to the user through a mobile application on a mobile device such as a tablet computer or smartphone. Treadmill gait training is known and easily implemented and preferred for that reason.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

What is claimed is:

1. A biofeedback rehabilitation display for gait training visible to the subject comprising:
    a plurality of foot placement targets configured to be visible to the subject on the display and configured for moving along the display at a speed proportional to the desired gait speed of the subject and in a direction along the display representative of the direction of locomotion of the subject;
    a pair of subject foot icons configured to be visible to the subject illustrating real-time foot positioning of the subject at all times throughout the gait pattern of the subject, wherein the foot icons distinguish between stance phase and swing phase throughout the gait pattern of the subject; and
    at least one real-time proximity measurement visible to the subject for each stance phase providing the subject with an indication of the proximity of the stance phase foot with an intended foot placement target.

2. The biofeedback rehabilitation display for gait training according to claim 1 wherein a stance phase is determined by the detection of a heel strike of the subject and the real-time proximity measurement is determined by the radial distance from a fixed point of the stance phase foot position to a fixed point on the nearest foot placement target.

3. The biofeedback rehabilitation display for gait training according to claim 1 wherein the real-time proximity measurement visible to the subject includes a visible indication when the proximity measurement is less than an acceptable threshold.

4. The biofeedback rehabilitation display for gait training according to claim 3 wherein the real-time proximity measurement visible to the subject includes a visible indication when the proximity measurement is greater than an unacceptable threshold.

5. The biofeedback rehabilitation display for gait training according to claim 4 wherein the real-time proximity measurement visible to the subject includes a visible indication when the proximity measurement is between the acceptable threshold and the unacceptable threshold.

6. The biofeedback rehabilitation display for gait training according to claim 3 wherein the foot placement target includes a visible representation of an associated proximity measurement.

7. The biofeedback rehabilitation display for gait training according to claim 1 wherein the real-time proximity measurement visible to the subject for each stance phase provide the subject with an indication of the proximity of each stance phase foot with an intended foot placement target in both the direction of locomotion of the subject and lateral to the direction of locomotion of the subject.

8. The biofeedback rehabilitation display for gait training according to claim 1 wherein a stance phase is determined by the detection of a heel strike of the subject and the stance phase illustrates foot orientation of the subject's foot at the time of the detected heel strike.

9. The biofeedback rehabilitation display for gait training according to claim 8 further including a visual indication of the difference between the measured foot orientation of the subject's foot and the target foot orientation of the subject's foot.

10. The biofeedback rehabilitation display for gait training according to claim 1 further including an audio component of the real-time proximity measurement which is audible to the subject.

11. The biofeedback rehabilitation display for gait training according to claim 1 wherein the speed of the foot placement targets is derived from a treadmill coupled to the display and wherein the speed of the foot placement targets is variable.

12. The biofeedback rehabilitation display for gait training according to claim 1 wherein the real-time foot positioning of the subject throughout the gait pattern of the subject is obtained through motion capture software.

13. The biofeedback rehabilitation display for gait training according to claim 12 wherein the motion capture software tracks position markers placed on the pelvis, lower limbs, and feet of the subject monitored by cameras.

14. The biofeedback rehabilitation display for gait training according to claim 1 wherein the spacing between adjacent foot placement targets visible to the subject is adjustable.

15. The biofeedback rehabilitation display for gait training according to claim 1 wherein a spacing between adjacent foot placement targets visible to the subject will vary for one subject to train gait adaptability.

16. The biofeedback rehabilitation display for gait training according to claim 15 wherein the variance of the spacing between adjacent foot placement targets visible to the subject for training gait adaptability include variance in mediolateral position and spacing in the direction of locomotion.

17. The biofeedback rehabilitation display for gait training according to claim 1 further including the display of virtual obstacles visible to the subject on the display and moving along the display at a speed proportional to the desired gait speed of the subject and in a direction along the display representative of the direction of locomotion of the subject.

18. The biofeedback rehabilitation display for gait training according to claim 17 further including the display of real-time proximity measurements visible to the subject for each virtual obstacle associated with a degree of avoidance of the virtual obstacle.

19. The biofeedback rehabilitation display for gait training according to claim 1 wherein the foot placement target includes a visible representation of an associated proximity measurement.

* * * * *